(12) United States Patent
Narita et al.

(10) Patent No.: US 7,282,549 B2
(45) Date of Patent: Oct. 16, 2007

(54) FLUORINE-CONTAINING COMPOUNDS, FLUORINE-CONTAINING POLYMERIZABLE MONOMERS, FLUORINE-CONTAINING POLYMERS, DISSOLUTION INHIBITORS, AND RESIST COMPOSITIONS

(75) Inventors: Tadashi Narita, Kanagawa (JP); Kazuhiko Maeda, Tokyo (JP)

(73) Assignee: Central Glass Company Limited, Ube-shi (JP)

( * ) Notice: Subject to any disclaimer, the term of this patent is extended or adjusted under 35 U.S.C. 154(b) by 0 days.

(21) Appl. No.: 10/753,071

(22) Filed: Jan. 8, 2004

(65) Prior Publication Data

US 2004/0192867 A1   Sep. 30, 2004

(30) Foreign Application Priority Data

Jan. 10, 2003   (JP) .............................. 2003-004262

(51) Int. Cl.
*C08F 118/00* (2006.01)

(52) U.S. Cl. .................. 526/242; 526/81; 526/245; 526/246; 526/247

(58) Field of Classification Search .............. 526/246, 526/245, 242, 247
See application file for complete search history.

(56) References Cited

U.S. PATENT DOCUMENTS

| | | | |
|---|---|---|---|
| 4,644,043 A * | 2/1987 | Ohmori et al. ............. | 526/246 |
| 6,013,752 A * | 1/2000 | Mowrer et al. ............... | 528/26 |
| 2002/0028886 A1* | 3/2002 | Abe et al. ................. | 525/326.3 |
| 2003/0232940 A1* | 12/2003 | Komoriya et al. .......... | 526/242 |

FOREIGN PATENT DOCUMENTS

EP    180913 A1 *  5/1986
WO   WO88/09799 *  12/1988

OTHER PUBLICATIONS

Theodore. H. Fedynshyn, et al., "Fluoroaromatic Resists for 157-nm Lithography", Journal of Polymer Science and Technology, 2002, pp. 655-666, vol. 15, No. 4, Lexington, MA.
Ralph R. Dammel et al., "New Resin Systems for 157 nm Lithography", Journal of Polymer Science and Technology, 2001, pp. 603-612, vol. 14, No. 4.

* cited by examiner

*Primary Examiner*—David W. Wu
*Assistant Examiner*—Henry S. Hu
(74) *Attorney, Agent, or Firm*—Crowell & Moring LLP

(57) ABSTRACT

The invention relates to a fluorine-containing compound containing a substituent represented by the formula 1:

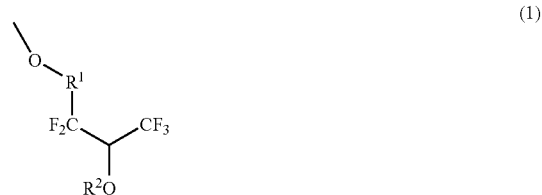

where $R^1$ is (a) a straight-chain alkylene group, (b) a branched alkylene group, (c) a cyclic structure containing an aromatic ring group or aliphatic cyclic group, or (d) a substituent containing an aromatic ring group and an aliphatic cyclic group, and $R^1$ optionally contains fluorine, another halogen, CN, oxygen, nitrogen, silicon, or alcohol, and $R^2$ is a hydrogen atom, a straight-chain or branched alkyl group, an aromatic group, or a hydrocarbon group optionally containing an aliphatic cyclic group, and $R^2$ optionally contains fluorine, oxygen, nitrogen, carbonyl bond, or alcohol, and a plural number of $R^2$ having different structures are optionally contained in the molecule.

15 Claims, No Drawings

FLUORINE-CONTAINING COMPOUNDS, FLUORINE-CONTAINING POLYMERIZABLE MONOMERS, FLUORINE-CONTAINING POLYMERS, DISSOLUTION INHIBITORS, AND RESIST COMPOSITIONS

BACKGROUND OF THE INVENTION

The present invention relates to (a) novel, fluorine-containing compounds containing a special structure, that is, a fluorinated acid hydroxyl group, which may be protected, (b) fluorine-containing polymerizable monomers containing the special structure, (c) fluorine-containing polymers prepared by polymerization or copolymerization of such compounds or monomers, (d) dissolution inhibitors using those, and (e) resist compositions using such fluorine-containing compounds, monomers, fluorine-containing polymers, and dissolution inhibitors.

Fluorine-containing compounds have been used or developed in various fields particularly in the field of advanced materials due to their good qualities (e.g., water repellency, oil repellency, low water absorption, heat resistance, weather resistance, corrosion resistance, transparency, photosensitivity, low refractive index, and low dielectric property). Recently, there have been active researches and developments of fluorine-containing compounds for resist compositions and the like due to their transparency in ultraviolet region, particularly in vacuum ultraviolet wavelength region. A common aim in polymer design of such researches and developments is to achieve good adhesion to substrate and high glass transition point (hardness), while achieving transparency in each wavelength for use by introducing as many fluorine atoms as possible. For example, in the case of using a high fluorine-content polymer that has been highly fluorinated by tetrafluoroethylene or a cyclic fluorine-containing monomer, transparency in each wavelength for use is known to increase. However, there are few reports on increasing etching resistance and adhesion of fluorine-containing monomers themselves.

Recently, in next generation $F_2$ resist field of vacuum ultraviolet region, there were reports on a hydroxyl-containing fluorostyrene (see T. H. Fedynyshyn, A. Cabral et al., J. Photopolym. Sci. Technol., 15, 655-666 (2002)) and on a hydroxyl-containing fluoronorbornene compound (see Ralph R. Dammel, Raj Sakamuri, et al., J. Photopolym. Sci. Technol., 14, 603-612 (2001)). Thus, there was emerged an idea of containing fluorine and making polarity of hydroxyl group coexistent in the molecule. However, most compounds based on such idea have disadvantages such as too high acid strength, too low glass transition point (Tg) and too low etching resistance, for example, due to their hexafluoroisopropanol (hexafluorocarbinol) structure or a secondary acid alcohol directly bonded to a cyclic fluororesin.

Although highly transparent fluororesins containing a secondary acid alcohol directly bonded to cyclic fluororesins have recently been developed, such fluororesins also have disadvantages such as too low etching resistance and too low dissolution rate upon development. Although there have been efforts for dissolving such disadvantages by nicely designing the resin skeleton, there has been a demand for the development of a fluorine-containing acid hydroxyl group containing a different structure. In other words, conventional resin skeletons are not necessarily enough in function, since they have many defects such as insufficient compatibility between transparency in ultraviolet region and etching resistance. Thus, there has been a demand for creating a novel monomer or raw material capable of providing further improved polymers, which are free of the above-mentioned defects.

SUMMARY OF THE INVENTION

It is therefore an object of the present invention to provide a novel fluorine-containing compound or fluorine-containing polymerizable monomer, which is capable of providing a fluorine-containing polymer that is high in transparency.

It is another object of the present invention to provide the fluorine-containing polymer prepared by a polymerization or copolymerization using the fluorine-containing polymerizable monomer.

It is a further object of the present invention to provide a dissolution inhibitor or resist composition by using the fluorine-containing polymerizable monomer or the fluorine-containing polymer.

According to the present invention, there is provided a fluorine-containing compound or fluorine-containing polymerizable monomer, comprising a substituent represented by the formula 1:

(1)

where $R^1$ is (a) a straight-chain alkylene group, (b) a branched alkylene group, (c) a cyclic structure containing an aromatic ring group or aliphatic cyclic group, or (d) a substituent containing an aromatic ring group and an aliphatic cyclic group, and $R^1$ optionally contains fluorine, another halogen, CN, oxygen, nitrogen, silicon, or alcohol (which may be defined as a hydrocarbon group having at least one hydroxyl group), and $R^2$ is a hydrogen atom, a straight-chain or branched alkyl group, an aromatic group, or a hydrocarbon group optionally containing an aliphatic cyclic group, and $R^2$ optionally contains fluorine, oxygen, nitrogen, carbonyl bond, or alcohol, and a plural number of $R^2$ having different structures are optionally contained in the molecule.

According to the present invention, there is provided a fluorine-containing polymer comprising the substituent represented by the formula 1.

According to the present invention, there is provided a dissolution inhibitor comprising a compound represented by the formula 5:

(5)

wherein $R^2$ is an acid-labile protecting group,
$R^3$ is a straight-chain or cyclic group containing at least one selected from the group consisting of ether bond, ester bond and hydroxyl group, and
m is an integer of 1-3.

According to the present invention, there is provided a resist composition comprising the fluorine-containing polymer.

DESCRIPTION OF THE PREFERRED EMBODIMENTS

The fluorine-containing compound or fluorine-containing polymerizable monomer according to the present invention, which contains a substituent (a novel fluorine-containing acid group) represented by the formula 1, contains a special polar group in the molecule while its fluorine content is high. With this, the polymer prepared by a polymerization or copolymerization of the fluorine-containing polymerizable monomer becomes high in transparency.

The inventors have successfully synthesized the above-mentioned fluorine-containing compound or fluorine-containing polymerizable monomer containing a novel fluorine-containing hydroxyl group (unexpectedly showing an acidity similar to that of a hexafluorocarbinol group) while its skeleton has only one $CF_3$ group. We further unexpectedly found that various monomers (e.g., acrylates, fluorine-containing acrylic acids, vinyl ethers, and allyl ethers), which are easy in industrial uses, can easily be derived from the fluorine-containing polymerizable monomer, that it is possible to synthesize a novel, special fluorine-containing polymer by a polymerization or copolymerization of the fluorine-containing polymerizable monomer, that the fluorine-containing polymer can exhibit special properties as a resist composition to be used in patterning of semiconductors and the like, and that the fluorine-containing compound, fluorine-containing polymerizable monomer or the fluorine-containing polymer can be used for dissolution inhibitors.

The fluorine-containing polymerizable monomer of the present invention may have the substituent (represented by the formula 1) at its side chain. Its examples include first polymerizable monomers (such as acrylic esters, methacrylic esters, α-$CF_3$ acrylic esters, and α-cyanoacrylic esters) represented by the formula 2:

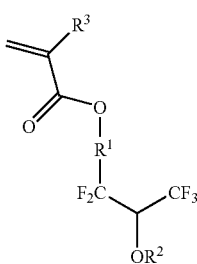

(2)

wherein $R^1$ and $R^2$ are defined as in the formula 1, and $R^3$ is a hydrogen, fluorine, alkyl group optionally containing fluorine, or cyano group.

Its examples further include second polymerizable monomers (vinyl ethers and allyl ethers) represented by the formula 3:

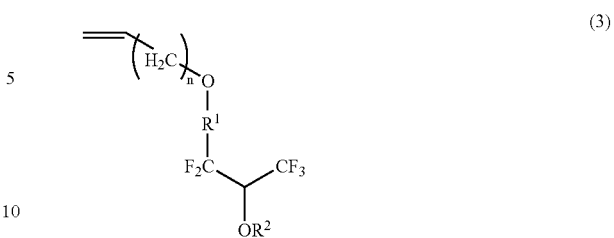

(3)

wherein $R^1$ and $R^2$ are defined as in the formula 1, and n is 0 or 1.

Its examples further include third polymerizable monomers containing in the molecule a polymerizable unsaturated bond (e.g., those of styrene, vinyl silane, olefins, vinyl esters, and norbornene) and a substituent represented by the formula 1.

The third polymerizable monomers may be norbornene compounds represented by the formula 7:

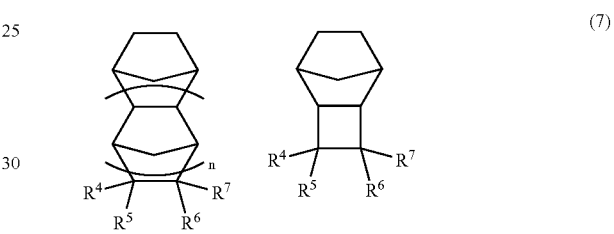

(7)

wherein each of $R^4$, $R^5$, $R^6$, and $R^7$ is independently a hydrogen, fluorine, another halogen, a straight-chain or branched alkyl or fluoroalkyl group optionally containing a cyclic structure, a fluorine-containing cyclic group, hydroxyl group, carboxyl group, a hydroxyl or carboxyl group protected with $R^2$ as defined in the formula 1, or a group containing at least two of these, and wherein at least one of $R^4$, $R^5$, $R^6$, and $R^7$ in each of the above two formulas 7 contains the structure (substituent) of the formula 1. The process for synthesizing such norbornene compounds is not particularly limited. These compounds may be synthesized by conducting a Diels-Alder reaction between the compound of the formula 2 or 3 and cyclopentadiene.

In the substituent represented by the formula 1, examples of $R^1$ include straight-chain or branched alkylene groups (e.g., methylene, ethylene, propylene, and isobutyrene), cyclic structures (e.g., cyclobutyl group, cyclohexyl group, phenyl group, norbornene group, adamantyl group, and cyclic lactone group), and combined substituents each containing at least two of these. A part of $R^1$ optionally contains fluorine, oxygen, nitrogen or silicon.

In the substituent represented by the formula 1, examples of $R^2$ include a hydrogen atom, a straight-chain or branched alkyl group, an aromatic group, and a hydrocarbon group optionally containing an aliphatic cyclic group. $R^2$ optionally contains fluorine, oxygen, nitrogen, carbonyl bond, or alcohol (which may be defined as a hydrocarbon group containing at least one hydroxyl group). Although the structure of $R^2$ is not particularly limited, it may basically be a hydrogen atom (—$OR^2$: a hydroxyl group), which provides the fluorine-containing polymer with high transparency. Depending on use of the target product, this hydrogen atom as $R^2$ may be replaced with one of the above-mentioned various groups. For example, $R^2$ may be a $C_1$-$C_{20}$ hydrocarbon group such as methyl group, ethyl group, isopropyl group, cyclopropyl group, t-butyl group, cyclopentyl group, cyclohexyl group, norbornel group, adamantyl group, methyladamantyl group, ethyladamantyl group, and benzyl group. Examples of $R^2$ containing oxygen atom are acyclic ether groups (e.g., methoxymethyl ether and methoxyethoxymethyl ether) and cyclic ethers (e.g., tetrahydrofuran and tetrahydropyran). Examples of $R^2$ as aromatic groups include 4-methoxybenzyl group. Examples of $R^2$ containing carbonyl group are acetyl group, pivaloyl group, tert-butoxycarbonyl group and benzoyl group. Examples of $R^2$ containing oxygen are carbonyl group and butyl lactone group. $R^2$ may be protected or modified with a nitrogen-containing substituent or the like. Such $R^2$ may contain fluorine atom, unsaturated bond, or the like. Furthermore, at least a part of $R^1$ may contain a hexafluorocarbinol group represented by the formula 6:

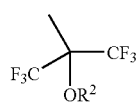

(6)

wherein $R^2$ is defined as in the formula 1.

In the substituent represented by the formula 1, $R^2$ may be a combination of a plurality of the above-mentioned substituents. Such $R^2$ may be substituents in which alkyl group, fluoroalkyl group, carbonyl group, hydroxyl group, carboxyl group and the like are bonded to alicyclic structures and aromatic rings. $R^2$ may partially or completely be fluorinated. Furthermore, $R^2$ may have at its terminal a particular fluorine-containing substituent such as hexafluorocarbinol group. The purposes of using the above-mentioned substituents as $R^2$ are to provide the target products with (a) solubility in organic solvents and alkali aqueous solutions, (b) high glass transition point, (c) photosensitivity due to acid-lability where the substituent is removed by a photoacid generator, (d) etching resistance due to cyclic structure, (e) adhesion to substrate, and the like. Thus, it is possible to select a suitable $R^2$ depending on the use of the target polymerizable monomer of the present invention. Furthermore, it is possible to use a plural number of $R^2$ having different structures at the same time.

In the following, an exemplary process for synthesizing a compound having a structure (substituent) of the formula 1 is explained. In this process, a compound of the formula 4:

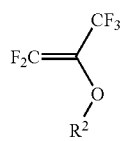

(4)

wherein $R^2$ is defined as in the formula 1, is reacted with $R^1OH$, $R^1OR^4$ or $R^3$ in the presence of peroxide. In the present invention, $R^1OH$ is not particularly limited as long as it is an alcohol. Preferable examples of $R^1OH$ are methanol, ethanol, isopropanol, butanol, ethylene glycol, propylene glycol, tetramethylene glycol, glycerol, cyclohexanol, norbornene alcohol, adamantyl alcohol, monovalent and polyvalent alcohols having other cyclic structures. A part of $R^1OH$ may contain ester bond and fluorine. Although R1OH may apparently be a monovalent alcohol, it may also be a polyvalent alcohol in which $R^1$ contains another OH group. Another reactant $R^1OR^4$ is a compound prepared by modifying $R^1OH$ with $R^4$ through an ether or ester bond, and it can be used in the above synthesis as a reactant analogous to $R^1OH$.

In the present invention, $R^3$ usable in the formulas 2 and 5 is not particularly limited. In the above-mentioned synthesis, $R^3$ may be selected from almost all compounds without particular limitation as long as they contain hydrocarbon groups, since an unsaturated bond in the compound of the formula 4 attacks a carbon-hydrogen bond in $R^3$ to effect an addition reaction. In case that $R^3$ contains an unsaturated bond group, the addition reaction may slow down or terminate. Therefore, such $R^3$ is not preferable in the above synthesis. $R^3$ usable in the formulas 2 and 5 may be an alcohol-free hydrocarbon or a partially fluorinated hydrocarbon. These hydrocarbons may contain a cyclic structure, ether or ester. In fact, preferable examples of such $R^3$ are alkanes (e.g., methane, ethane, propane, and butane), cyclic compounds (e.g., norbornane, adamantane, and cyclohexane), alkyl ethers (e.g., methyl ether, ethyl ether, and propylene glycol), propylene glycol methyl ether acetate, tetrahydrofuran, dioxane, oxonorbornane, lactone, cyclic lactone, ethers optionally containing cyclic structures, epoxy compounds, and esters.

By conducting a radical addition reaction using a compound of the formula 4, it is possible to produce a compound of the formula 5:

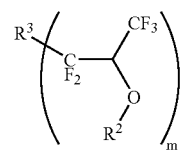

(5)

wherein $R^2$ is defined as in the formula 1,
$R^3$ is a straight-chain or cyclic group containing at least one selected from the group consisting of ether bond, ester bond and hydroxyl group, and
m is an integer of 1-3.

In case that an alcoholic compound is selected for at least a part of $R^3$ in the formula 5, the structure of the formula 5 becomes the same as that of the formula 1.

It is possible to obtain polymerizable monomers (e.g., acrylic esters, methacrylic esters, α-fluoroalkylacrylic esters, and α-cyanoacrylic esters) represented by the formula 2 by an esterification of an alcohol moiety of the compound of the formula 1 or 5. In contrast, it is possible to obtain polymerizable monomers (e.g., vinyl ethers and allyl ethers) represented by the formula 3 by adding a polymerizable unsaturated bond through an ether bond. For example, it is possible by using isopropyl alcohol as $R^1OH$ to synthesize the following polymerizable monomers:

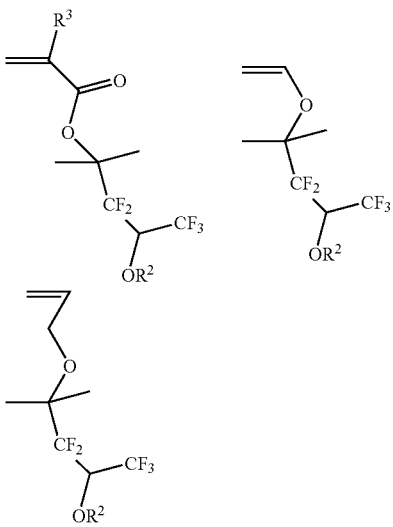

wherein $R^2$ and $R^3$ are respectively defined as in the formulas 1 and 2.

Furthermore, it is possible by using dioxane as $R^3$ to obtain the following polymerizable monomers:

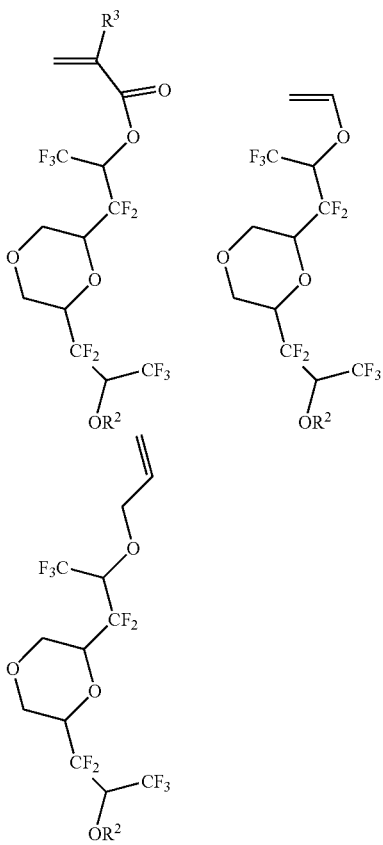

wherein $R^2$ and $R^3$ are respectively defined as in the formulas 1 and 2.

In the invention, it is possible to obtain various fluorine-containing polymerizable monomers, based on a radical addition reaction in which a fluorine-containing compound of the formula 4 is added to a part of a reactant selected from alcohols, ethers, and esters.

An exemplary process for producing the fluorine-containing polymerizable monomer by reacting a compound of the formula 4 with a hydrocarbon is explained, as follows. At first, a sealed reaction vessel was sealingly charged with a reactant (i.e.: an alcohol, ether or ester represented by $R^1OH$ or $R^3$ and optionally having a cyclic structure), a fluorine-containing unsaturated compound of the formula 4 (e.g., 2-benzoxypentafluoropropene represented by the following formula), and a radical initiator.

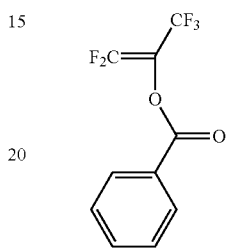

Then, a radical addition reaction was conducted at a temperature of 0-150° C., preferably 30-120° C. After terminating the reaction, a compound of the formula 5 is isolated by ordinary purification operations such as concentration, washing and distillation. Then, fluorine-containing polymerizable monomers are derived from the obtained compound of the formula 5. A radical initiator usable in the radical addition reaction can be selected from compounds similar to those for a polymerization initiator. Oxides (e.g., t-butylperoxypivalate and benzoyl peroxide) can be used as preferable radical initiators without any limitation.

In the invention, homopolymers or copolymers can be derived from the fluorine-containing polymerizable monomer of the formula 2 or 3. Comonomers for producing the copolymers are not particularly limited, as long as they have copolymerizability with the monomer of the formula 2 or 3. Examples of such comonomers include olefins, fluorine-containing olefins, acrylic esters, methacrylic esters, fluorine-containing acrylic esters, fluorine-containing methacrylic esters, norbornene compounds, fluorine-containing norbornene compounds, styrene compounds, fluorine-containing styrene compounds, vinyl ethers, fluorine-containing vinyl ethers, vinyl esters, fluorine-containing vinyl esters, allyl ethers, fluorine-containing allyl ethers, and vinyl silanes.

Exemplary olefins for the above-mentioned comonomer include ethylene and propylene. Exemplary fluorine-containing olefins for that are vinyl fluoride, vinylidene fluoride, trifluoroethylene, chlorotrifluoroethylene, tetrafluoroethylene, hexafluoropropylene, hexafluoroisobutene, and octafluorocyclopentene.

Exemplary (meth)acrylic esters (i.e., acrylic esters and methacrylic esters) for the above-mentioned comonomer are not particularly limited with respect to their ester side chains. They are (meth)acrylic alkyl esters such as methyl (meth)acrylate, ethyl(meth)acrylate, n-propyl(meth)acrylate, isopropyl(meth)acrylate, n-butyl(meth)acrylate, isobutyl(meth)acrylate, n-hexyl(meth)acrylate, n-octyl(meth)acrylate, 2-ethylhexyl(meth)acrylate, lauryl(meth)acrylate, 2-hydroxyethyl(meth)acrylate, and 2-hydroxypropyl(meth)acrylate; (meth)acrylates containing groups such as ethylene glycol, propylene glycol and tetramethylene glycol; unsaturated amides such as (meth)acrylic amide, N-methylol (meth)acrylic amide, and diacetoneacrylic amide; (meth) acrylonitrile, alkoxysilane-containing vinyl silanes and (meth)acrylic esters, tert-butyl(meth)acrylate, and cyclic (meth)acrylate such as 3-oxocyclohexyl(meth)acrylate, adamantyl(meth)acrylate, alkyladamantyl(meth)acrylate, cyclohexyl(meth)acrylate, tricyclodecanyl(meth)acrylate and (meth)acrylate having cyclic structures such as lactone ring and norbornene ring; and (meth)acrylic acid. Further examples are (meth)acrylate containing a cyano group at α-position and analogous compounds such as maleic acid, fumaric acid and maleic anhydride.

The fluorine-containing (meth)acrylic esters for the above-mentioned comonomer may have a fluorine atom or fluorine-containing group at their α-position or may have a substituent having a fluorine atom at ester moiety. Such fluorine-containing groups at their α-position may be trifluoromethyl group, trifluoroethyl group and nonafluoro-n-butyl group.

Further exemplary fluorine-containing (meth)acrylic esters as the above-mentioned comonomer may have at their ester moiety a fluoroalkyl or perfluoroalkyl group or a fluorine-containing cyclic structure. This cyclic structure may have a substituent (e.g., fluorine atom and trifluoromethyl group), and its examples are fluorine-containing benzene ring, fluorine-containing cyclopentane ring, fluorine-containing cyclohexane ring, and fluorine-containing cycloheptane ring. Further exemplary (meth)acrylic esters may have at their ester moiety a fluorine-containing t-butyl ester group. Specific examples of the fluorine-containing (meth)acrylic ester are 2,2,2-trifluoroethyl(meth)acrylate, 2,2,3,3-tetrafluoropropyl(meth)acrylate, 1,1,1,3,3,3 -hexafluoroisopropyl(meth)acrylate, heptafluoroisopropyl(meth)acrylate, 1,1-dihydroheptafluoro-n-butyl(meth)acrylate, 1,1,5-trihydrooctafluoro-n-pentyl(meth)acrylate, 1,1,2,2 -tetrahydrotridecafluoro-n-octyl(meth)acrylate, 1,1,2,2 -tetrahydroheptadecafluoro-n-decyl(meth)acrylate, and perfluorocyclohexylmethyl(meth)acrylate.

Further examples of the above-mentioned comonomer are monomers having a trifluoro or hexafluorocarbinol group at their side chain terminal to be acid and monomers protected with acid-labile protecting groups and other functional groups. These monomers are not particularly limited in structure. The above-mentioned norbornene compounds and fluorine-containing norbornene compounds as examples of the comonomer may have a mononucleus or multinucleus structure.

It is possible to prepare the norbornene compounds by a Diels-Alder addition reaction of unsaturated compounds (e.g., fluorine-containing olefin, allyl alcohol, fluorine-containing allyl alcohol, acrylic acid, □-fluoroacrylic acid, methacrylic acid, and all of the above-mentioned (meth) acrylic esters and fluorine-containing (meth)acrylic esters) to dienes (e.g., cyclopentadiene and cyclohexadiene). The norbornene compounds may be those having a trifluoro or hexafluorocarbinol group at their side chain terminal to have acidity and may be those protected with acid-labile protecting groups and other functional groups. Those norbornene compounds are not particularly limited in structure.

Further examples of the above-mentioned comonomer are styrene compounds and fluorine-containing styrene compounds, such as styrene, fluorinated styrene, hydroxystyrene, and a styrene compound in which a hexafluorocarbinol group(s) is bonded to the benzene ring. In other words, the comonomer can preferably be selected from fluorine-containing styrene and hydroxystyrene, each containing fluorine atom or trifluoromethyl group substituted for hydrogen, and styrene compounds containing a halogen, an alkyl group or a fluorine-containing alkyl group at their α-position.

Still further examples of the above-mentioned comonomer are vinyl ethers and fluorine-containing vinyl ethers. Although these two kinds of vinyl ethers may be inferior in copolymerizability with the fluorine-containing polymerizable monomer of the present invention, they can be used in the copolymerization depending on their amount relative to the fluorine-containing polymerizable monomer. For example, the comonomer may be an alkyl vinyl ether that optionally contains methyl group, ethyl group, or hydroxyl group (e.g., hydroxyethyl group or hydroxybutyl group). Furthermore, the comonomer may be a cyclic vinyl ether containing a cyclohexyl group or a hydrogen or carbonyl bond in its cyclic structure. Furthermore, the comonomer may be a fluorine-containing vinyl ether, which contains fluorine substituted for hydrogen of an unsaturated bond, or a perfluorovinyl ether. Still furthermore, the comonomer may be selected from allyl ethers, vinyl esters, and vinyl silanes without any particular limitation upon use as long as they are known compounds. Furthermore, vinyl ethers and allyl ethers as the comonomers may be those having a trifluoro or hexafluorocarbinol group at their side chain terminal to be acid and those protected with acid-labile protecting groups and other functional groups without limitation in their structures. These comonomers may be used alone or in combination of at least two.

Upon the polymerization, the ratio of the fluorine-containing polymerizable monomer to the comonomer is not particularly limited. The amount of the former is preferably from 10-100%, more preferably 20-100%. If it is less than 20%, the resulting polymer may become insufficient in acid strength or transparency.

The polymerization or copolymerization method for obtaining the target polymer (copolymer) is not particularly limited. For example, it is preferable to use radical polymerization or ionic polymerization. In some cases, it is also possible to use coordinated anionic polymerization or living anionic polymerization.

Particulars of the above-mentioned radical polymerization are as follows. The radical polymerization can be conducted by a known manner such as bulk polymerization, solution polymerization, suspension polymerization or emulsion polymerization by a batch-wise, half-continuous or continuous operation.

The radical polymerization initiator is not particularly limited. Its examples are azo compounds, peroxides and redox compounds. Of these, preferable ones are azobisbutyronitrile (AIBN), t-butylperoxypivalate, di-t-butylperoxide, i-butyrylperoxide, lauroylperoxide, succinic acid peroxide, dicinnamylperoxide, di-n-propylperoxydicarbonate, t-butylperoxyallyl monocarbonate, benzoyl peroxide, hydrogen peroxide, and ammonium persulfate.

The reaction vessel for conducting the polymerization (copolymerization) is not particularly limited. It is optional to use a solvent for conducting the polymerization. The polymerization solvent is preferably one that does not interfere with the radical polymerization. Its typical examples are esters such as ethyl acetate and n-butyl acetate; ketones such as acetone and methyl isobutyl ketone; hydrocarbons such as toluene and cyclohexane; and alcohols such as isopropyl alcohol and ethylene glycol monomethyl ether. Furthermore, it can be selected from various other solvents such as water, ethers, cyclic ethers, fluorohydrocarbons, and aromatic solvents. It is optional to use a single solvent or a mixture of at least two solvents. Furthermore, it is possible to use a molecular weight adjusting agent, such as mercaptan, in the polymerization. The temperature for conducting the polymerization may be suitably adjusted depending on the type of radical polymerization initiator or radical polymerization initiating source. It is preferably 0-200° C., particularly preferably 30-140° C.

After the polymerization, it is possible to remove the reaction medium (i.e., organic solvent or water) from the solution or dispersion of the target polymer by a known method. For example, it can be conducted by reprecipitation followed by filtration, or by heating under vacuum to distill the medium off. The target polymer according to the present invention may have a number average molecular weight of 1,000-100,000, preferably 3,000-50,000. The polymer of the present invention in the form of a thin film (thickness: about 100 nm) has a transmittance of about 60% or more with respect to 157 nm $F_2$ laser.

The resist composition of the present invention can be used for both of negative-type and positive-type resist compositions, of which solubility in alkali aqueous solution changes by the action of acid. The resist compositions of the present invention are preferably used as negative-type, positive-type or other photoresists, for example, for preparing semiconductors using a 193 nm ArF excimer laser, a vacuum ultraviolet (typically 157 nm) $F_2$ laser, electron beam or X-ray. The resist composition of the present invention may be more effectively used as a positive-type resist composition. In this case, the polymer, of which solubility in alkali aqueous solution changes by the action of acid, is characterized, for example, in that $R^2$ of the polymerizable monomer or the comonomer has an acid-labile protecting group. Such polymer is insoluble or very slightly soluble in alkali aqueous solution prior to the activating energy ray irradiation. The activating energy ray irradiation, however, generates an acid from the acid generator. Then, the polymer is hydrolyzed by this acid and thereby becomes soluble in alkali aqueous solution. In contrast, in the case of a negative-type resist composition, the polymer may be characterized in that it becomes insoluble in a developing agent by the activating energy ray irradiation through a crosslinking reaction between the resins.

The dissolution inhibitor having a structure of the formula 5 is explained, as follows. This dissolution inhibitor of the present invention is not particularly limited as long as it has a structure of the formula 5. From the viewpoint of etching resistance, it is preferable that $R^3$ is a ring structure and $R^2$ is an acid-labile protecting group. For example, the dissolution inhibitor may have the following exemplary structures:

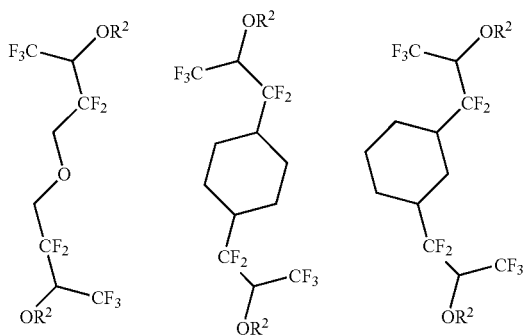

wherein each $R^2$ is independently defined as in the formula 1.

The above-mentioned acid generator for a resist composition is not particularly limited. It can be suitably selected from acid generators for chemically amplified resists. Examples of such acid generators are bissulfonyldiazomethanes, nitrobenzyl derivatives, onium salts, halogen-containing triazine compounds, cyano group-containing oximesulfonate compounds, and other oximsulfonate compounds. The acid generator may be used in the form of a single compound or a mixture of at least two compounds. The content of the acid generator in the resist composition may be 0.5-20 parts by weight, relative to 100 parts by weight of the polymer. If it is less than 0.5 parts by weight, the resist composition may become insufficient in image forming capability. If it is greater than 20 parts by weight, it may become difficult to prepare a uniform solution of the resist composition. Thus, the resulting solution may become inferior in storage stability.

The above-mentioned resist composition according to the present invention can be used in conventional resist patterning methods, as exemplified in the following. Firstly, a solution of the resist composition is applied to a supporting member (e.g., silicon wafer) by spin coating or the like, followed by drying to form a photosensitive layer. Then, the photosensitive layer is exposed to a laser light from an exposure apparatus through a desired mask pattern, followed by heating. Then, a development treatment is conducted by using, for example, an alkali aqueous solution such as 0.1-10 wt % tetramethylammonium hydroxide aqueous solution, thereby obtaining a resist pattern conforming to the mask pattern.

According to need, it is optional to add a miscible additive to the polymer. Examples of such additive are additional resins, quencher, plasticizer, stabilizer, coloring agent, surfactant, tackifier, leveling agent, deforming agent, compatibility enhancing agent, adhesion enhancing agent, and antioxidant.

The following nonlimitative examples are illustrative of the present invention.

EXAMPLE 1

A stainless steel, pressure-proof autoclave was charged with 472 g of isopropyl alcohol (IPA), 252 g of 2-benzoxypentafluoropropene, and 40 g of benzoyl peroxide. The internal atmosphere of the autoclave was evacuated and replaced with nitrogen three times. Then, the reaction was conducted at 80° C. for 48 hr and then at 100° C. for 20 hr. After cooling, the reaction product was purified by distillation, thereby obtaining 212 g of a first fluorine-containing compound (identified with NMR) represented by the following formula:

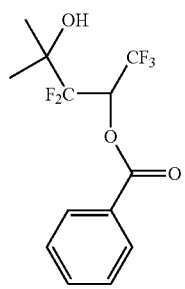

1st Fluorine-containing Compound

EXAMPLE 2

A stainless steel, pressure-proof autoclave was charged with 600 g of dioxane (DOX), 252 g of 2-benzoxypentafluoropropene (BPFP), and benzoyl peroxide. Then, the internal atmosphere of the autoclave was evacuated and replaced with nitrogen three times. Then, the reaction was conducted at 80° C. for 5 days. After cooling, the reaction product was purified by distillation, thereby obtaining 420 g of a second fluorine-containing compound (identified with NMR) represented by the following formula. Furthermore, the following third and fourth fluorine-containing compounds were respectively obtained by repeating the above procedure except in that dioxane was replaced with ethyl alcohol and cyclohexanehexafluorocarbinol.

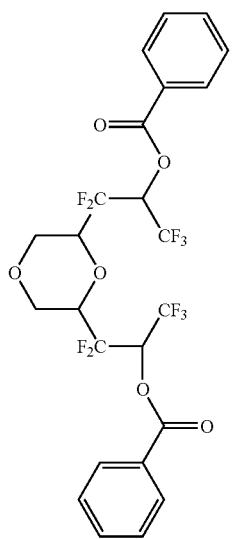

2nd Fluorine-containing Compound

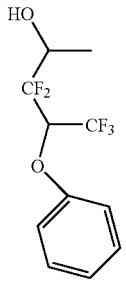

3rd Fluorine-containing Compound

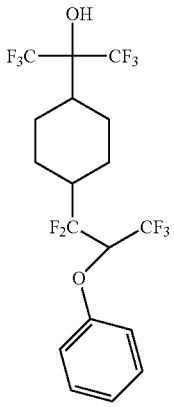

4th Fluorine-containing Compound

EXAMPLE 3

The first to fourth fluorine-containing compounds obtained by Examples 1 and 2 were respectively subjected to hydrolysis at room temperature for 4 hr in the presence of $K_2CO_3$, water and methanol, thereby obtaining fifth to eighth fluorine-containing compounds represented by the following formulas.

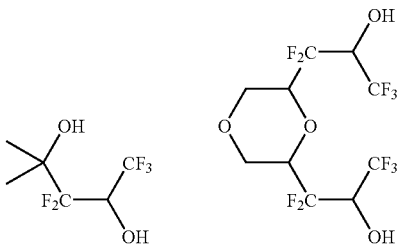

5th Compound        6th Compound

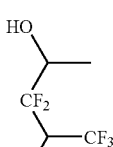 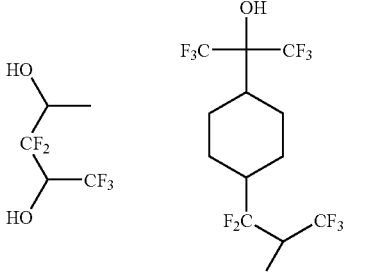

7th Compound        8th Compound

EXAMPLE 4

An esterification between the 6th fluorine-containing compound obtained by Example 3 and α-CF3 acrylic chloride was conducted as follows to obtain a 4th monomer represented by the formula hereinbelow. At first, 10 g of the 6th fluorine-containing compound were dissolved at room temperature in methylene chloride in a four-necked 500 ml flask. After adding 9.7 ml of triethylamine, 14 g of 2-trifluoromethylacrylic chloride were added in a dropwise manner by spending 5 min under cooling with ice, followed by stirring at room temperature for 1 hr. Under cooling with ice, a suitable amount of saturated ammonium chloride aqueous solution was added to decompose an excess of the reagent, followed by extraction of an organic matter with diethyl ether. Then, the obtained organic layer was washed with ion-exchanged water and saturated brine. Then, the obtained organic layer was dried with magnesium sulfate, followed by concentration under vacuum with an evaporator, thereby obtaining the 4th monomer.

EXAMPLE 5

The 7th fluorine-containing compound was reacted with ethyl vinyl ether as follows, thereby synthesizing the monomer represented by the formula hereinbelow. Prior to the synthesis, a catalyst was prepared as follows. A 100 mL glass vessel was charged with 11.2 g of palladium acetate and 1 L of toluene to prepare a solution. Then, 200 mL of a toluene solution containing 8 g of bipyridyl were gradually added, followed by stirring for 10 min. The obtained precipitate was filtered, followed by washing with ether and then recrystallization from 500 mL dichloromethane. 3 hours later, the precipitated crystals were separated by filtration, followed by vacuum drying for 12 hr, thereby preparing a Pd catalyst. Then, a 100 mL glass vessel was charged with 2.3 g of the 7th fluorine-containing compound, 0.19 g of the Pd catalyst, and 19 mL of ethyl vinyl ether, followed by stirring for 24 hr under cooling with water bath. Then, the reaction mixture was filtered through Cellite, followed by washing with water and saturated brine, drying with anhydrous magnesium sulfate, and distilling the solvent off, thereby obtaining 1.3 g of the third monomer through silica gel chromatography. Similar to Example 4 and the above synthesis of he third monomer, there were obtained first, second, fifth and sixth monomers represented by the following formulas.

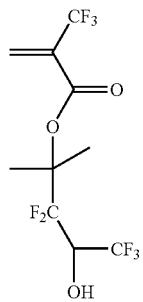
1st Monomer

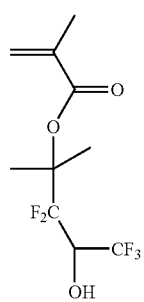
2nd Monomer

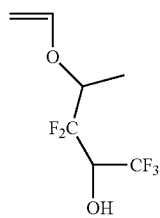
3rd Monomer

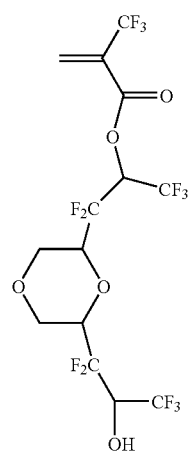
4th Monomer

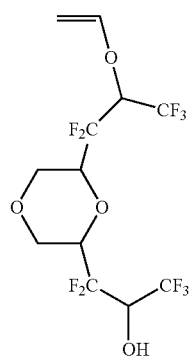
5th Monomer

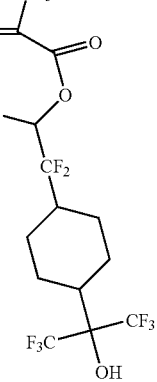
6th Monomer

EXAMPLE 6

Acid-labile protecting groups were introduced into terminals of the first and fifth monomers of the above formulas, thereby respectively obtaining seventh and eighth polymerizable monomers 7 and 8 represented by the formulas hereinbelow. Similarly, acid-labile protecting groups were introduced into both terminals of the sixth fluorine-containing compound, thereby obtaining a dissolution inhibitor (DI) represented by the following formula.

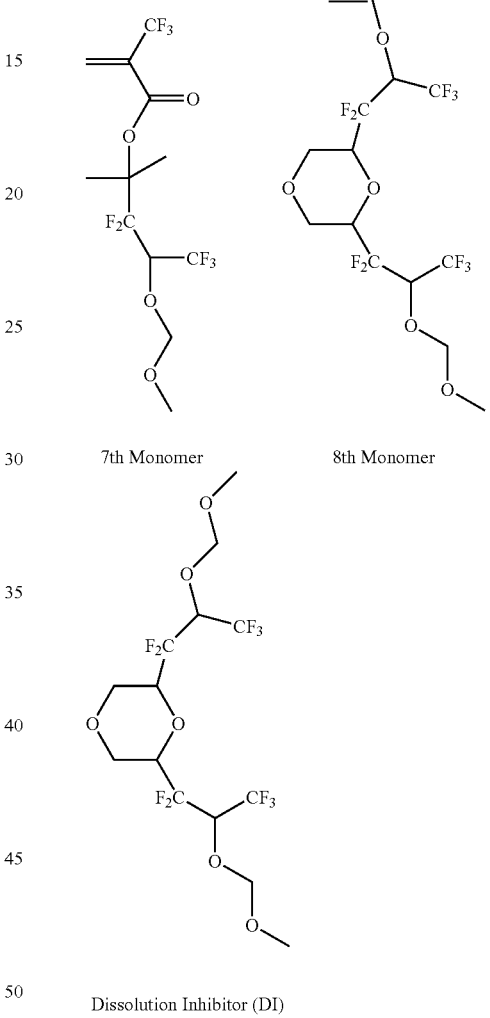

7th Monomer          8th Monomer

Dissolution Inhibitor (DI)

EXAMPLE 7

In a three-necked flask equipped with a reflux condenser and a stirrer, 99 g of the first monomer, 79 g of TFMA-B represented by the formula hereinbelow, and 82 g of BTHB-NB represented by the formula hereinbelow were mixed together with 500 g of n-butyl acetate, thereby preparing a solution. Then, 7 g of azobisbutyronitrile (AIBN) were added as a polymerization initiator, followed by heating with an oil bath of 60° C. Under this condition, the reaction was conducted for 20 hr. After the reaction, the obtained reaction solution was added to a large excess of n-hexane, followed by stirring. The resulting precipitate was separated by filtration and then dried under vacuum at 50° C. for 18 hr. The obtained polymer composition (the first polymer) was found by $^1$H-NMR and $^{19}$F-NMR to be 38 wt % of the first monomer, 32 wt % of TFMA-B and 30 wt % of BTHB-NB. Its weight average molecular weight (Mw) was determined by gel permeation chromatography (GPC) using polystyrene as a standard. The results of Examples 7-9 are shown in Table.

EXAMPLE 8

The radical polymerization of Example 7 was repeated except in that the first monomer was replaced with each of the second to eighth monomers, thereby obtaining second to eighth polymers shown in Table. Furthermore, a propylene glycol monomethyl ether solution of each of the first, third to sixth, and eighth polymers was prepared, and this solution was applied to a CaF$_2$ plate to form a thin film of about 100 nm. Then, the transmittance of each film at 157 nm was measured. Similarly, a propylene glycol monomethyl ether solution of each of the second and seventh polymers was prepared, and this solution was applied to a CaF$_2$ plate to form a thin film of about 300 nm. Then, the transmittance of each film at 193 nm was measured. The results are shown in Table. The abbreviations in Table correspond to compounds represented by the following formulas.

TABLE

|  | 1st polymer | 2nd polymer | 3rd polymer | 4th polymer | 5th polymer | 6th polymer | 7th polymer | 8th polymer | 9th polymer | 10th polymer |
|---|---|---|---|---|---|---|---|---|---|---|
| Polymer Composition | | | | | | | | | | |
| 1st monomer | 38 | | | | 45 | | | | | 38 |
| 2nd monomer | | 48 | | | | | | | | |
| 3rd monomer | | | | | | 19 | 20 | 40 | | |
| 4th monomer | | | 21 | | | | | | | |
| 5th monomer | | | 22 | | | | | | | |
| 6th monomer | | | | 44 | | | | | | |
| 7th monomer | | | 30 | | | | 30 | | | |
| 8th monomer | | | 27 | | | | | 60 | | |
| Dissolution Inhibitor | | | | | | | | | 30 | 20 |
| TFMA-B | 32 | | | | | | | | | 32 |
| BTHB-NB | 30 | | | | 25 | | | | 100 | 30 |
| BTHB-NB-MOM | | | | | | 32 | | | | |
| 3,5-HFA-ST | | | | | | | | | | |
| 3,5-HFA-ST-MOM | | | | 56 | | | | | | |
| TFMA-BTHB-NB | | | | | | | 19 | | | |
| MA-MAD | | 52 | | | | | | 38 | | |
| MA-BL | | | | | | | | 42 | | |
| TFE | | | | | | 30 | | | | |
| Polymer Properties | | | | | | | | | | |
| Mw | 16000 | 19000 | 15000 | 11000 | 17000 | 11000 | 18000 | 9800 | 14000 | 16000 |
| Transmittance (157 nm) | 65% | | 76% | 63% | 72% | 67% | | 84% | 74% | 77% |
| Transmittance (193 nm) | | 85% | | | | | 80% | | | |

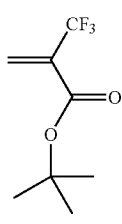

TFMA-B

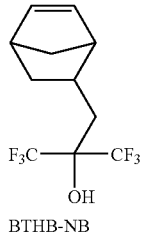

BTHB-NB

TABLE-continued
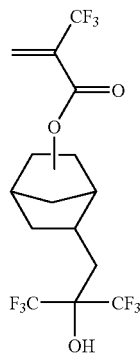
TFMA-BTHB-NB
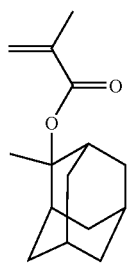
MA-MAD
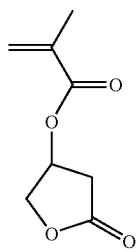
MA-BL
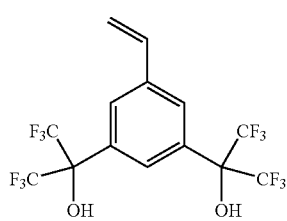
3,5-HFA-ST
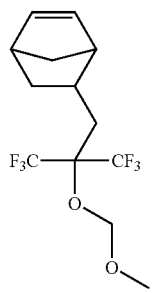
BTHB-NB-MOM TABLE-continued

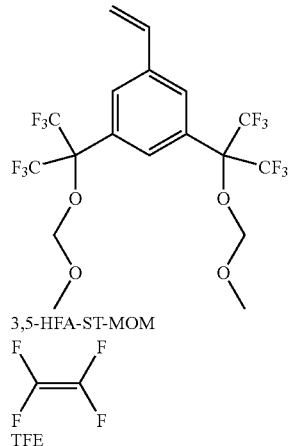

3,5-HFA-ST-MOM

F F
\\=/
F F
TFE

EXAMPLE 9

Each of the first to eighth polymers (fluorine-containing copolymers) was dissolved in propylene glycol monomethyl ether to have a total solid matter concentration of 15 wt %. Then, 2 parts by weight of triphenylsulfoniumtrifluoromethanesulfonate (as an acid generator) and 0.5 parts by weight of tri-n-octylamine, based on 100 parts by weight of each of the first to eighth fluorine-containing copolymers, were dissolved in the solution, followed by filtration with a membrane filter (pore diameter: 0.2 µm), thereby respectively preparing first to eighth resist solutions. A ninth resist solution was prepared in the same manner as above except in that 30 parts by weight of the aforementioned dissolution inhibitor (DI), based on 100 parts by weight of a homopolymer of BTHB-NB, were additionally dissolved in the solution. In other words, a combination of a homopolymer of BTHB-NB and DI refers to the ninth polymer. Furthermore, a tenth resist solution was prepared in the same manner as above except in that 20 parts by weight of the aforementioned dissolution inhibitor (DI), based on 100 parts by weight of the first polymer, were additionally dissolved in the solution. In other words, a combination of the first polymer and DI refers to the tenth polymer. Then, each of the first to tenth resist solutions was applied to a silicon wafer (widths: 6 inches) by spin coating to form a thin film (thickness: 150 nm), followed by drying at 80° C., thereby forming first to tenth films. Each of these films was found to be insoluble in 2.38 wt % tetramethylammonium hydroxide aqueous solution. Then, each film was subjected to a preliminary baking at 80° C. for 60 seconds, followed by exposure to KrF excimer laser (248 nm) and then a post exposure baking at 120° C. for 120 seconds. The resulting each film was dissolved in 2.38 wt % tetramethylammonium hydroxide aqueous solution (developing solution). Each resist pattern obtained by the development had no development defects. In other words, each of the first to tenth polymers were proved to be capable of providing a good positive-type resist behavior and resist pattern.

The entire disclosure of Japanese Patent Application No. 2003-004262 (filed on Jan. 10, 2003), which is a basic Japanese patent application of the present application, including specification, claims and summary, is incorporated herein by reference in its entirety.

What is claimed is:

1. A fluorine-containing polymerizable monomer comprising a substituent represented by the formula 1,

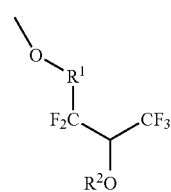

(1)

where $R^1$ is (a) a straight-chain alkylene group, (b) a branched alkylene group, (c) a cyclic structure containing an aromatic ring group or aliphatic cyclic group, or (d) a substituent containing an aromatic ring group and an aliphatic cyclic group, and $R^1$ optionally contains fluorine, another halogen, CN, oxygen, nitrogen, silicon, or alcohol, and $R^2$ is a hydrogen atom, a straight-chain or branched alkyl group, an aromatic group, or a hydrocarbon group optionally containing an aliphatic cyclic group, and $R^2$ optionally contains fluorine, oxygen, nitrogen, carbonyl bond, or alcohol, and a plural number of $R^2$ having different structures are optionally contained in the molecule.

2. A fluorine-containing polymerizable monomer according to claim 1, which is represented by the formula 2,

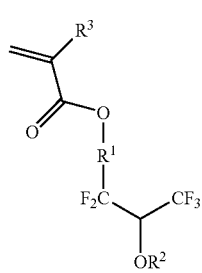

(2)

wherein $R^1$ and $R^2$ are defined as in the formula 1, and $R^3$ is a hydrogen, fluorine, alkyl group optionally containing fluorine, or cyano group.

3. A fluorine-containing polymerizable monomer according to claim 1, which is represented by the formula 3,

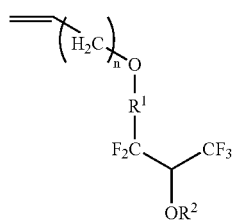

(3)

wherein $R^1$ and $R^2$ are defined as in the formula 1, and n is 0 or 1.

4. A fluorine-containing polymerizable monomer according to claim 1, wherein the substituent represented by the formula 1 is derived from a compound represented by the formula 5,

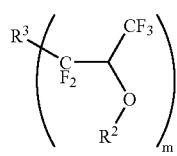

(5)

wherein $R^2$ is defined as in the formula 1, $R^3$ is a straight-chain or cyclic group containing at least one selected from the group consisting of ether bond, ester bond and hydroxyl group, and m is an integer of 1-3, wherein the compound represented by the formula 5 is prepared by a radical addition reaction, in which a compound represented by the formula 4:

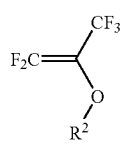

(4)

wherein $R^2$ is defined as in the formula 1, is added to an alcohol, ether or ester compound.

5. A fluorine-containing polymerizable monomer according to claim 1, wherein $R^2$ in the formula 1 is an acid-labile protecting group.

6. A fluorine-containing polymerizable monomer according to claim 1, wherein $R^1$ is a bivalent group comprising a hexafluorocarbinol group represented by the formula 6,

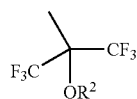

(6)

wherein $R^2$ is defined as in the formula 1.

7. A fluorine-containing polymerizable monomer according to claim 1, which is selected from first to eighth fluorine-containing polymerizable monomers respectively represented by the following formulas M1 to M8:

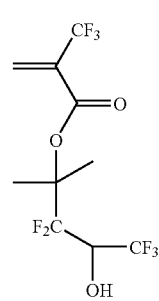

M1

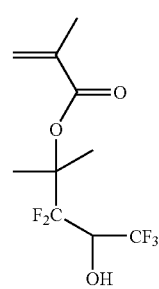

M2

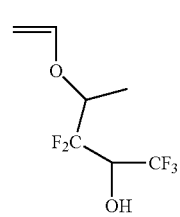

M3

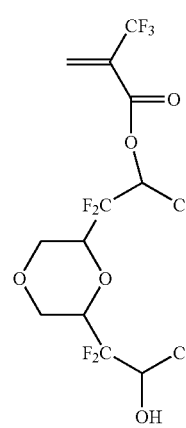

M4

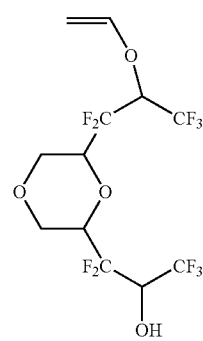

M5

-continued

M6
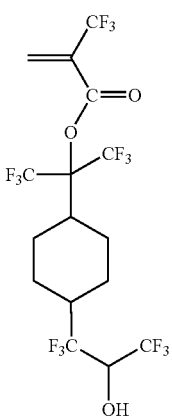

M7
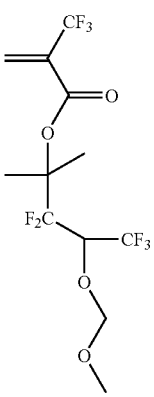

M8
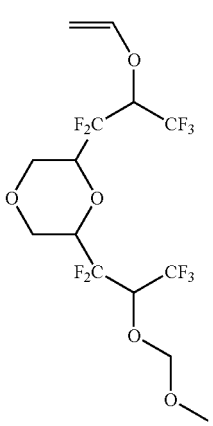

8. A fluorine-containing polymer comprising a substituent represented by the formula 1, (1)
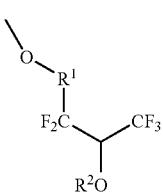

where $R^1$ is (a) a straight-chain alkylene group, (b) a branched alkylene group, (c) a cyclic structure containing an aromatic ring group or aliphatic cyclic group, or (d) a substituent containing an aromatic ring group and an aliphatic cyclic group, and $R^1$ optionally contains fluorine, another halogen, CN, oxygen, nitrogen, silicon, or alcohol, and $R^2$ is a hydrogen atom, a straight-chain or branched alkyl group, an aromatic group, or a hydrocarbon group optionally containing an aliphatic cyclic group, and $R^2$ optionally contains fluorine, oxygen, nitrogen, carbonyl bond, or alcohol, and a plural number of $R^2$ having different structures are optionally contained in the molecule.

9. A fluorine-containing polymer according to claim 8, which is prepared by a polymerization or copolymerization, using a fluorine-containing polymerizable monomer comprising the substituent represented by the formula 1, and wherein the fluorine-containing polymerizable monomer is represented by the formula 2 or 3:

(2)
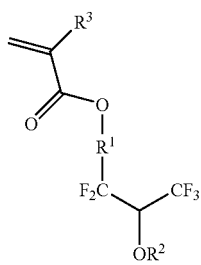

wherein $R^1$ and $R^2$ are defined as in the formula 1, and
$R^3$ is a hydrogen, fluorine, alkyl group optionally containing fluorine, or cyano group.

(3)
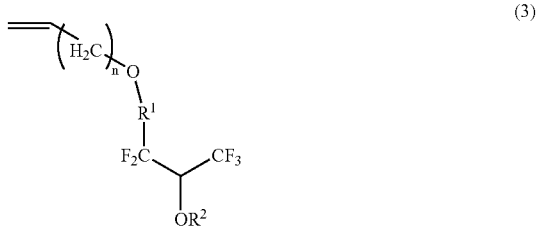

wherein $R^1$ and $R^2$ are defined as in the formula 1, and n is 0 or 1.

10. A fluorine-containing polymer according to claim 8, wherein $R^1$ is a bivalent group comprising a hexafluorocarbinol group represented by the formula 6, (6)
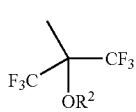

wherein $R^2$ is defined as in the formula 1.

11. A fluorine-containing polymer according to claim 9, wherein the fluorine-containing polymerizable monomer, which is used in the copolymerization, comprises a hexafluorocarbinol group represented by the formula 6, (6)

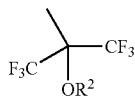

wherein R² is defined as in the formula 1.

12. A fluorine-containing polymer according to claim 9, wherein the fluorine-containing polymerizable monomer comprises a norbornene represented by one of the following two formulas 7, (7)

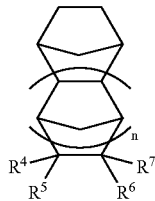 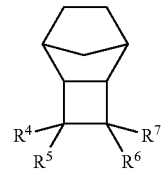

wherein each of R⁴, R⁵, R⁶, and R⁷ is independently a hydrogen, fluorine, another halogen, a straight-chain or branched alkyl or fluoroalkyl group optionally containing a cyclic structure, a fluorine-containing cyclic group, hydroxyl group, carboxyl group, a hydroxyl or carboxyl group protected with R² as defined in the formula 1, or a group containing at least two of these.

13. A fluorine-containing polymer according to claim 9, wherein R² in the formula 2 or 3 is an acid-labile protecting group.

14. A fluorine-containing polymer according to claim 8, which comprises a repeating unit derived from at least one monomer selected from first to eighth fluorine-containing polymerizable monomers respectively represented by the following formulas M1 to M8:

M1

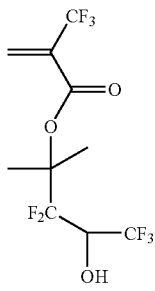

M2

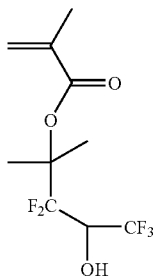

-continued

M3

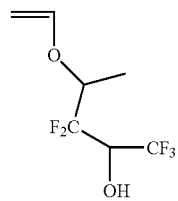

M4

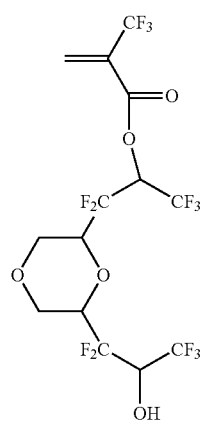

M5

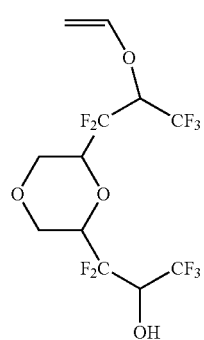

M6

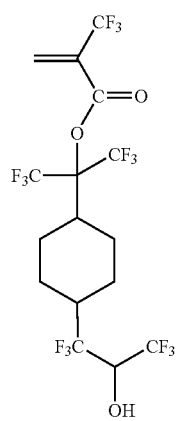

-continued
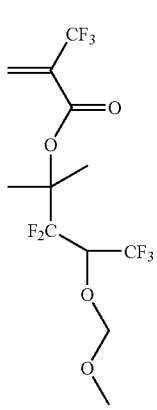
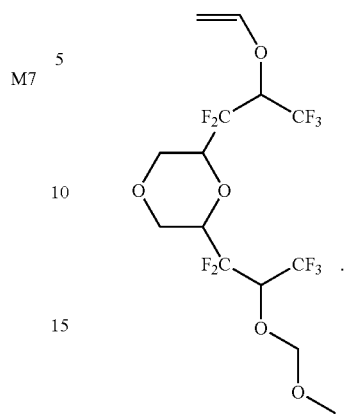
M7
M8
15. A resist composition comprising a fluorine-containing polymer according to claim 8.
* * * * *